United States Patent [19]

Guillaumet et al.

[11] Patent Number: 5,061,713
[45] Date of Patent: Oct. 29, 1991

[54] ANALGESIC OXAZOLOPYRIDINE COMPOUNDS

[75] Inventors: Gérald Guillaumet; Christine Flouzat, both of Orleans; Jacqueline Bonnet, Paris, all of France

[73] Assignee: Science et Organization, Neuilly-sur-Seine, France

[21] Appl. No.: 564,033

[22] Filed: Aug. 7, 1990

[30] Foreign Application Priority Data

Aug. 7, 1989 [FR] France .................. 89 10596

[51] Int. Cl.$^5$ .................. A61K 31/435; C07D 498/04
[52] U.S. Cl. .................. 514/302; 546/115; 546/116
[58] Field of Search .................. 546/115, 116; 514/302

[56] References Cited

U.S. PATENT DOCUMENTS 4,038,396 7/1977 Shen et al. .................. 546/115

Primary Examiner—Bernard Dentz
Attorney, Agent, or Firm—Gordon W. Hueschen

[57] ABSTRACT

Compound of general formula (I):

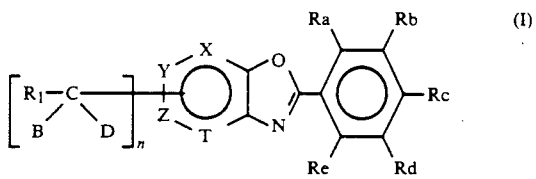

in which:

X, Y, Z and T each represent, independently of one another, a nitrogen atom, a —CH= group or a group CW, in which W represents a halogen atom or a lower alkyl or alkoxy group optionally substituted with one or more halogen atoms, such as a trifluoromethyl group, on condition that only one of them represents a nitrogen atom, Ra, Rb, Rc, Rd and Re represent, independently of one another, a hydrogen atom, a halogen atom or a lower alkyl or alkoxy group optionally substituted with one or more halogen atoms, such as a trifluoromethyl group, B represents a hydrogen atom and D a hydroxyl group, or B and D simultaneously represent an oxygen atom, n represents 1 or 2, and $R_1$ represents a hydrogen atom, a linear or branched lower alkyl, linear or branched lower alkenyl, aryl or lower arylalkyl group or a cycloalkyl group having 3 to 7 carbon atoms, it being possible for each of the lower alkyl, lower alkenyl, aryl, lower arylalkyl and cycloalkyl groups to be substituted with one or more halogen atoms or a lower alkyl or alkoxy group optionally substituted with one or more halogen atoms, such as a trifluoromethyl group, their isomers, epimers and diastereoisomers, and addition salts with a pharmaceutically acceptable acid are useful in the treatment of pain.

17 Claims, No Drawings

ANALGESIC OXAZOLOPYRIDINE COMPOUNDS

The present invention relates to new oxazolo[4,5]-or -[5,4]pyridine compounds, to a process for preparing them and to pharmaceutical compositions containing them.

The properties, both analgesic and anti-inflammatory, of 2-phenyloxazolo[5,4]- and -[4,5]pyridines are already known (U.S. Pat. No. 4,038,396, FR 2,328,471, FR 2,319,354, GB 1,421,619).

However, these products possess an essentially anti-inflammatory profile, as confirmed by the therapeutic indications mentioned in the patents cited above, or else have the drawback of not dissociating the two types of activity: analgesic on the one hand, antipyretic and anti-inflammatory on the other hand.

The Applicant has now discovered new compounds whose level of analgesic activity is at least comparable, or even superior, to that of the already known 2-phenyloxazolo[4,5-b]pyridines, but possessing the especially advantageous feature of being completely devoid of anti-inflammatory activity: the compounds of the present invention are, in effect, endowed with a high-level pure analgesic activity. In point of fact, most non-morphinic analgesic substances known to date also possess anti-inflammatory activity (for example salicyl compounds, pyrazole compounds, etc.), and they consequently intervene in the processes occurring in inflammation. These processes involve a very large number of chemical mediators (prostaglandins, thomboxane A2, etc.); multifarious side effects accordingly ensue, the best known of which are: attack of the gastric mucosa with the possibility of ulcers, and inhibition of platelet aggregation with disorders of coagulation. Apart from the disturbances they cause, these concomitant effects prohibit the use of these products in many subjects who are especially sensitive to them. Being devoid of all anti-inflammatory activity, the compounds of the present invention hence do not interact with the mediators of inflammation, and are hence devoid of the side effects mentioned above. This feature, combined with their complete absence of toxicity and their high level of activity, renders the compounds of the present invention usable as an analgesic much more safely and without the restrictions in use customarily known for the large majority of these products.

More specifically, the invention relates to compounds of general formula (I):

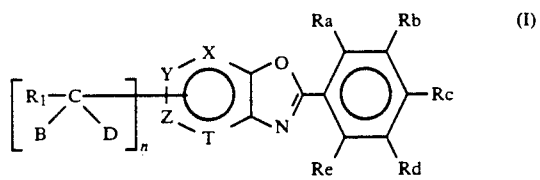

in which:
X, Y, Z and T each represent, independently of one another, a nitrogen atom, a —CH= group or a group CW or CV, in which V and W, which may be identical or different, represent a halogen atom or a linear or branched lower alkyl or alkoxy group optionally substituted with one or more halogen atoms, such as a trifluoromethyl group, on condition that only one of them represents a nitrogen atom, Ra, Rb, Rc, Rd and Re represent, independently of one another, a hydrogen atom, a halogen atom or a linear or branched lower alkyl or alkoxy group optionally substituted with one or more halogen atoms, such as a trifluoromethyl group, B represents a hydrogen atom and D a hydroxyl group, or B and D simultaneously represent an oxygen atom, n represents 1 or 2, and $R_1$ represents a hydrogen atom, a linear or branched lower alkyl, linear or branched lower alkenyl, aryl or lower arylalkyl group, a cycloalkyl group having 3 to 7 carbon atoms or a cycloalkylalkyl group, it being possible for each of the lower alkyl, lower alkenyl, aryl, lower arylalkyl, cycloalkyl and cycloalkylalkyl groups to be substituted with one or more halogen atoms or a lower alkyl or alkoxy group optionally substituted with one or more halogen atoms, such as a trifluoromethyl group, their isomers, epimers and diastereoisomers, as well as their addition salts with a pharmaceutically acceptable acid.

Among acids which may be added to the compounds of formula (I) to form an addition salt, hydrochloric, sulfuric, phosphoric, tartaric, malic, maleic, fumaric, oxalic, methanesulfonic, ethanesulfonic, camphoric and citric acids, etc., may be mentioned by way of example.

Heteroaryl group is understood to mean aromatic groups containing one or more hetero atoms, such as thienyl, pyridyl, furyl and quinolyl.

At present, among the compounds of the invention, preference is given to those among which:
n represents 1,
on the one hand, T represents a nitrogen atom, X, Y and Z representing, independently of one another, a —CH= group or a group CV or CW, the group $R_1$—C(BD) being bound to the carbon X or Z,
on the other hand, X represents a nitrogen atom and Y, Z and T represent a —CH= group or a group CV or CW, the group $R_1$—C (BD) being bound to the carbon T or Y.

The invention also encompasses the process for obtaining the compounds of formula (I), wherein: either a compound of general formula (II):

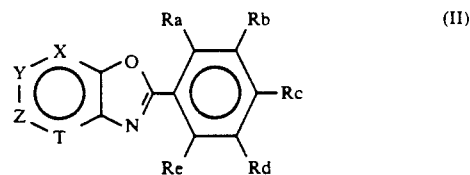

described in British Patent 1,421,619, or a compound of general formula (III):

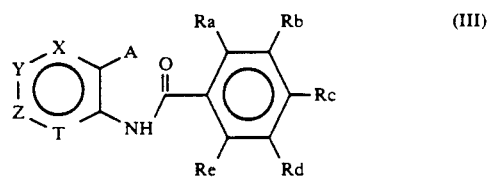

in which compounds X, Y, Z, T, Ra, Rb, Rc, Rd and Re have the same meaning as in formula (I) and A represents a halogen atom, is used as a starting material, which compounds are treated with a large excess of a product of formula (IV):

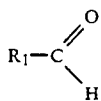

in which $R_1$ has the same meaning as in the formula (I), in an acid medium preferably obtained with a mixture of acetic acid and sulfuric acid, the reaction medium thereby obtained then being cooled to a temperature of between 0° C. and 15° C., and preferably between +2° C. and +5° C., stirred for about fifteen minutes and then treated with aqueous ferrous sulfate solution and tert-butyl hydroperoxide, stirred again for approximately one hour, diluted with water and treated with an aqueous solution of an alkali metal sulfite, preferably sodium sulfite, to obtain a product of general formula (I) in which B and D simultaneously represent an oxygen atom and in which n represents 1, which is optionally separated from a less abundant compound in which n represents 2 by a conventional separation technique, when a compound of formula (II) is used as a starting material, a product of general formula (V):

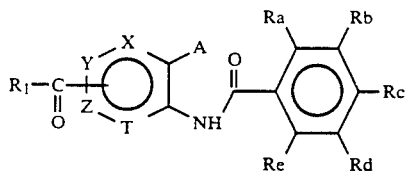

in which A, $R_1$, X, Y, Z, T, Ra, Rb, Rc, Rd and Re have the same meaning as above, when a compound of formula (III) is used as a starting material, a solution of which compound of formula (V), preferably in a halogenated solvent, is brought to reflux for a period preferably of between 10 and 24 hours in the presence of trimethylsilyl polyphosphate to lead to a compound of formula (I) in which B and D simultaneously represent an oxygen atom, which compound of formula (I), irrespective of the process according to which it has been obtained, is optionally separated into its isomers and purified by one or more techniques selected from extraction with an organic solvent, crystallization or chromatography on a silica column, and salified, if so desired, with a pharmaceutically acceptable acid, and which, in the case where B represents a hydrogen atom and D a hydroxyl group, is dissolved in a lower aliphatic alcohol and subjected to catalytic reduction with an alkali metal mixed hydride, such as sodium borohydride, to lead, after optional separation of the isomers and purification by chromatography, extraction and/or recrystallization, to a compound of formula (I) in which B represents a hydrogen atom and D a hydroxyl group, which is salified, if so desired, with a pharmaceutically acceptable acid.

The compounds of formula (V) are new and form part of the invention, in the same way as the compounds of formula (I) for which they constitute the synthesis intermediates.

The compounds of formula (I) possess advantageous pharmacological properties.

In particular, these compounds have evinced an advantageous analgesic activity.

A pharmacological study of the compounds of the invention showed, in effect, that they were of low toxicity, endowed with a pure analgesic activity and hence devoid of drawbacks inherent in most non-morphinic compounds exhibiting this activity (ulcerogenic action on the mucosae, interference with coagulation, etc.). This spectrum of activity hence renders the compounds of the present invention advantageous in a number of indications such as rheumatic pain, lumbosciatic neuralgia, cervicobrachial neuralgia, pain associated with trauma such as sprains, fractures, dislocations, post-traumatic pain, postoperative pain, dental pain, neurological pain such as facial neuralgia, visceral pain such as nephritic colic, dysmenorrhea, proctological surgery, pain of the ENT region, pancreatitis, various pains, headache, cancer pain, etc.

The subject of the present invention is also pharmaceutical compositions containing the products of formula (I) as well as their addition salts with a pharmaceutically acceptable acid, alone or in combination with one or more pharmaceutically acceptable, non-toxic, inert vehicles or excipients.

Among the pharmaceutical compositions according to the invention, there may be mentioned, more especially, those which are suitable for oral, parenteral and nasal administration, simple or sugar-coated tablets, sublingual tablets, sachets, packets, hard gelatin capsules, sublingual preparations, pills, suppositories, creams, ointments, skin gels, and the like.

The appropriate dosage varies according to the patient's age and weight, the administration route and the nature of the therapeutic indication and of any associated treatments, and ranges between 1 centigram and 4 grams per 24 hours.

The examples which follow illustrate the invention and in no way limit the latter.

The $^1H$ nuclear resonance magnetic spectra were recorded using TMS as an internal reference.

The infrared spectra were run using a potassium bromide disk containing 1% of the test product.

EXAMPLE 1

2-PHENYL-5-BUTYRYLOXAZOLO[4,5-b]PYRIDINE 0.005 mol (0.98 g) of 2-phenyloxazolo[4,5-b]pyridine and 0.03 mol (2.16 g) of freshly distilled butanal are mixed under argon.

A solution composed of 7.5 ml of acetic acid and 1.5 ml of concentrated sulfuric acid in 7.5 ml of water is added. The solution is cooled to a temperature in the region of 3° C. and, after 15 minutes, a solution of 8.34 g (0.03 mol) of $FeSO_4.7H_2O$ in 15 ml of water and 2 ml (0.021 mol) of 70% tert-butyl hydroperoxide are added simultaneously.

The mixture is left stirring for one hour and is diluted with water, and 10 ml of 10% sodium sulfite solution are added.

The precipitate obtained is filtered off, washed with water and dissolved in methylene chloride. It is washed several times with potassium bicarbonate solution. The organic phase is dried over magnesium sulfate. It is evaporated on a waterbath under vacuum, removing the excess aldehyde, and the product is purified by chromatography on 40 to 63μ silica (70-230 mesh);

eluent: ether/toluene, 2.5:7.5. It is recrystallized in ethanol.

Yield: 35%

Spectral characteristics: see Table 1.

EXAMPLE 2

2-PHENYL-7-BUTYRYLOXAZOLO[4,5-b]PYRIDINE

The procedure is as in Example 1; chromatography on silica gel (40–63μ; 70–230 mesh; eluent: ether/toluene: 2.5:7.5) carried out at the end of the synthesis enables, in fact, 2-phenyl-7-butyryloxazolo[4,5-b]pyridine to be separated from 2-phenyl-5-butyryloxazolo[4,5-b]pyridine.

Yield: 55%

Melting point: 147°–148° C.

Spectral characteristics: see Table 1.

EXAMPLES 3 TO 10

Using the procedure described in Examples 1 and 2, but replacing 2-phenyloxazolo[4,5-b]pyridine by 2-(halophenyl)oxazolo[4,5-b]pyridines, 2-(halophenyl)-5-butyryloxazolo[4,5-b]pyridines and 2-(halophenyl)-7-butyryloxazolo[4,5-b]pyridines are obtained.

EXAMPLES 3 AND 4

2-(4-CHLOROPHENYL)-5-BUTYRYLOXAZOLO[4,5-b]PYRIDINE

Example 3

Yield: 35%.

2-(4-CHLOROPHENYL)-7-BUTYRYLOXAZOLO[4,5-b]PYRIDINE

Example 4

Yield: 50%

Melting point: 139°–140° C. obtained using 2-(4-chlorophenyl)oxazolo[4,5-b]pyridine as a starting material.

EXAMPLES 5 AND 6

2-(2-FLUOROPHENYL)-b 5-BUTYRYLOXAZOLO[4,5-b]PYRIDINE

Example 5

Yield: 35%
Melting point: 138°–139° C.

2-(2-FLUOROPHENYL)-7-BUTYRYLOXAZOLO[4,5-b]PYRIDINE

Example 6

Yield: 55%

Melting point: 118°–119° C. obtained using 2-(2-fluorophenyl)oxazolo[4,5-b]pyridine as a starting material.

EXAMPLES 7 AND 8

2-(2-CHLOROPHENYL)-5-BUTYRYLOXAZOLO[4,5-b]PYRIDINE

Example 7

Yield: 25%
Melting point: 153°–154° C.

2-(2-CHLOROPHENYL)-7-BUTYRYLOXAZOLO[4,5-b]PYRIDINE

Example 8

Yield: 70%

Melting point: 113°–114° C. obtained using 2-(2-chlorophenyl)oxazolo[4,5-b]pyridine as a starting material.

EXAMPLES 9 AND 10

2-(2,6-DICHLOROPHENYL)-5-BUTYRYLOXAZOLO[4,5-b]PYRIDINE

Example 9

2-(2,6-DICHLOROPHENYL)-7-BUTYRYLOXAZOLO[4,5-b]PYRIDINE

Example 10

Yield: 30%

Melting point: 150° C. obtained using 2-(2,6-dichlorophenyl)oxazolo[4,5-b]pyridine as a starting material (chromatographic elution solvent: ether/toluene, 1:9).

EXAMPLES 11 AND 12

Using the procedure described in Examples 1 and 2, but replacing 2-phenyloxazolo[4,5-b]pyridine by 2-(2,6-difluorophenyl)oxazolo[4,5-b]pyridine and using 1.5 ml of concentrated sulfuric acid in 7.5 ml of water and 25 ml of acetic acid, and after chromatography on silica gel (40 to 63μ; 70 to 230 mesh; eluent: ethyl acetate/toluene, 1:9), the following are obtained:

2-(2,6-DIFLUOROPHENYL)-7-BUTYRYLOXAZOLO[4,5-b]PYRIDINE

Example 11

Recrystallization: cyclohexane
Melting point: 128°–129° C.

2-(2,6-DIFLUOROPHENYL)-5,7-DIBUTYRYLOXAZOLO[4,5-b]PYRIDINE

Example 12

Recrystallization: absolute ethanol
Melting point: 145° C.
Spectral characteristics:

$^1$H NMR δ (ppm) solvent CDCl$_3$: δ=1.05 ppm: 3H, triplet, CDCl$_3$; δ=1.09 ppm: 3H, triplet, CH$_3$; δ=8.61 ppm: 1H, singlet, H$_6$.

Infrared: 1685: ν (C=O); 1590: ν (C=C).

The physicochemical characteristics relating to Examples 3 to 11 appear in Table 1.

EXAMPLES 13 TO 16

Using the procedure described in Examples 5 to 8, but replacing butanal by benzaldehyde, the following are obtained:

2-(2-FLUOROPHENYL)-5-BENZOYLOXAZOLO[4,5-b]PYRIDINE

Example 13

Yield: 16%, tripled by doubling of the quantity of sulfuric acid introduced, i.e. 48%

Melting point: 149°–150° C.

2-(2-FLUOROPHENYL)-7-BENZOYLOXAZOLO[4,5-b]PYRIDINE

Example 14

Yield: 45%, unchanged if the quantity of sulfuric acid introduced is doubled.
Melting point: 130°–131° C.

2-(2-CHLOROPHENYL)-5-BENZOYLOXAZOLO[4,5-b]PYRIDINE

Example 15

Yield: 35%
Melting point: 148°–149° C.

2-(2-CHLOROPHENYL)-7-BENZOYLOXAZOLO[4,5-b]PYRIDINE

Example 16

Yield: 50%
Melting point: 129°–130° C.
The spectral characteristics of Examples 13 to 16 appear in Table 2.

EXAMPLES 17 TO 21
2-ARYL-5- or -7-(1-HYDROXYBUTYL)OXAZOLO[4,5-b]PYRIDINES 0.02 mmol of the selected 2-aryl-5(or 7)-butyryloxazolo[4,5-b]pyridine is placed in 200 cm$^3$ of methanol. 0.04 mmol of sodium borohydride is added slowly and with stirring. The mixture is stirred for 1 hour at room temperature. The methanol is evaporated off on a waterbath under vacuum, the residue is taken up with 100 cm$^3$ of water and the product is extracted with methylene chloride. The organic phase is evaporated and the residue is filtered off on a silica column (eluent: methylene chloride).

EXAMPLE 17
2-(2-FLUOROPHENYL)-7-(1-HYDROXYBUTYL)OXAZOLO[4,5-b]PYRIDINE

Recrystallization solvent: ether/cyclohexane
Melting point: 94°–95° C.
Spectral characteristics:
$^1$H NMR ($\delta$ ppm), solvent: CDCl$_3$; $\delta$=0.99: 3H, triplet, CH$_3$; $\delta$=1.48: 2H, multiplet, CH$_2$—CH$_3$; $\delta$=1.96: 2H, multiplet, CHOH—CH$_2$; $\delta$=2.53: 1H, doublet of doublet, OH; $\delta$=5.27: 1H, triplet, CH—OH; $\delta$=7.39: 1H, doublet: H$_6$, J=5 Hz; $\delta$=8.55: 1H, doublet: H$_5$, J=5 Hz.
Infrared $\nu$ (cm$^{-1}$): 3230: $\nu$ (OH) broad; 1690: $\nu$ (C=C).

EXAMPLE 18
2-PHENYL-5-(1-HYDROXYBUTYL)OXAZOLO[4,5-b]PYRIDINE.

EXAMPLE 19
2-PHENYL-7-(1-HYDROXYBUTYL)OXAZOLO[4,5-b]PYRIDINE.

EXAMPLE 20
2-(4-CHLOROPHENYL)-5-(1-HYDROXYBUTYL)OXAZOLO[4,5-b]PYRIDINE.

EXAMPLE 21
2-(4-CHLOROPHENYL)-7-(1-HYDROXYBUTYL)OXAZOLO[4,5-b]PYRIDINE.

EXAMPLES 22 TO 25
2-PHENYL-5- or -7-[PHENYL(HYDROXY)METHYL]OXAZOLO[4,5-b]PYRIDINES.

Using the procedure described in Examples 17 to 21, but replacing the 2-aryl-5(or 7)-butyryloxazolo[4,5-b]pyridines by the corresponding 2-aryl-5(or 7)-benzoyloxazolo[4,5-b]pyridines, the following are obtained:

EXAMPLE 22
2-PHENYL-5-[PHENYL(HYDROXY)METHYL]OXAZOLO[4,5-b]PYRIDINE

EXAMPLE 23
2-PHENYL-7-[PHENYL(HYDROXY)METHYL]OXAZOLO[4,5-b]PYRIDINE

EXAMPLE 24
2-(4-CHLOROPHENYL)-5-[PHENYL(HYDROXY)METHYL]OXAZOLO[4,5-b]PYRIDINE

EXAMPLE 25
2-(4-CHLOROPHENYL)-7-[PHENYL(HYDROXY)METHYL]OXAZOLO[4,5-b]PYRIDINE

EXAMPLES 26 TO 29

Using the same procedure as in Examples 1 and 2, but using cyclohexanecarbaldehyde instead of butanal, the following are obtained:
2-PHENYL-5-CYCLOHEXYLCARBONYLOXAZOLO[4,5-b]PYRIDINE (Example 26)
and:
2-PHENYL-7-CYCLOHEXYLCARBONYLOXAZOLO[4,5-b]PYRIDINE (EXAMPLE 27)
and, by reduction in the same manner as in Examples 17 to 21, the corresponding alcohols (Examples 28 and 29).

EXAMPLES 30 TO 35

Using the same procedure as in Examples 1 and 2, but using:
meta-tolualdehyde instead of butanal, the following are obtained:
2-PHENYL-5-[(3-METHYLPHENYL)CARBONYL]OXAZOLO[4,5-b]PYRIDINE (EXAMPLE 30);
2-PHENYL-7-[(3-METHYLPHENYL)CARBONYL]OXAZOLO[4,5-b]PYRIDINE (EXAMPLE 31);
para-trifluorotolualdehyde, the following are obtained:
2-PHENYL-5-[(4-TRIFLUOROMETHYLPHENYL)CARBONYL]OXAZOLO[4,5-b]PYRIDINE (EXAMPLE 32);
2-PHENYL-7-[(4-TRIFLUOROMETHYLPHENYL)CARBONYL]OXAZOLO[4,5-b]PYRIDINE (EXAMPLE 33);
2-thiophenecarbaldehyde, the following are obtained:
2-PHENYL-5-(2-THIENYLCARBONYL)OXAZOLO[4,5-b]PYRIDINE (EXAMPLE 34);
2-PHENYL-7-(2-THIENYLCARBONYL)OXAZOLO[4,5-b]PYRIDINE (EXAMPLE 35);
2-pyridinecarbaldehyde, the following are obtained:
2-PHENYL-5-(2-PYRIDYLCARBONYL)OXAZOLO[4,5-b]PYRIDINE (EXAMPLE 36);

2-PHENYL-7-(2-PYRIDYLCARBONYL)OXAZOLO[4,5-b]PYRIDINE (EXAMPLE 37);

3-quinolinecarbaldehyde, the following are obtained:
2-PHENYL-5-(3-QUINOLYLCARBONYL)OXAZOLO[4,5-b]PYRIDINE (EXAMPLE 38);
2-PHENYL-7-(3-QUINOLYLCARBONYL)OXAZOLO[4,5-b]PYRIDINE (EXAMPLE 39);

furfural, the following are obtained:
2-PHENYL-5-(2-FURYLCARBONYL)OXAZOLO[4,5-b]PYRIDINE (EXAMPLE 40);
2-PHENYL-7-(2-FURYLCARBONYL)OXAZOLO[4,5-b]PYRIDINE (EXAMPLE 41);

Using the procedure described in Examples 1 and 2, but using as a starting material:

2-(2-methoxyphenyl)oxazolo[4,5-b]pyridine, the following are obtained:
2-(2-METHOXYPHENYL)-5-BUTYRYLOXAZOLO[4,5-b]PYRIDINE (EXAMPLE 42);
2-(2-METHOXYPHENYL)-7-BUTYRYLOXAZOLO[4,5-b]PYRIDINE (EXAMPLE 43);

2-(3-methylphenyl)oxazolo[4,5-b]pyridine, the following are obtained:
2-(3-METHYLPHENYL)-5-BUTYRYLOXAZOLO[4,5-b]PYRIDINE (EXAMPLE 44);
2-(3-METHYLPHENYL)-7-BUTYRYLOXAZOLO[4,5-b]PYRIDINE (EXAMPLE 45);

2-(4-trifluoromethylphenyl)oxazolo[4,5-b]pyridine, the following are obtained:
2-(4-TRIFLUOROMETHYLPHENYL)-5-BUTYRYLOXAZOLO[4,5-b]PYRIDINE (EXAMPLE 46);
2-(4-TRIFLUOROMETHYLPHENYL)-7-BUTYRYLOXAZOLO[4,5-b]PYRIDINE (EXAMPLE 47);

2-(2,3,5-trichlorophenyl)oxazolo[4,5-b]pyridine, the following are obtained:
2-(2,3,5-TRICHLOROPHENYL)-5-BUTYRYLOXAZOLO[4,5-b]PYRIDINE (EXAMPLE 48);
2-(2,3,5-TRICHLOROPHENYL)-7-BUTYRYLOXAZOLO[4,5-b]PYRIDINE (EXAMPLE 49);

6-methyl-2-phenyloxazolo[4,5-b]pyridine, the following are obtained:
2-PHENYL-6-METHYL-5-BUTYRYLOXAZOLO[4,5-b]PYRIDINE (EXAMPLE 50);
2-PHENYL-6-METHYL-7-BUTYRYLOXAZOLO[4,5-b]PYRIDINE (EXAMPLE 51).

EXAMPLE 52

2-(2-FLUOROPHENYL)-5-METHYL-7-BUTYRYLOXAZOLO[4,5-b]PYRIDINE

Using the procedure described in Example 1, but replacing -phenyloxazolo[4,5-b]pyridine by 2-(2-fluorophenyl)-5-methyloxazolo[4,5-b]pyridine and using 1.5 ml of sulfuric acid, 5 ml of acetic acid (and not 7.5 ml) and 5 ml of water (and not 7.5 ml), and on purification by chromatography on silica gel (40 to 63μ; 70-230 mesh; eluent: ethyl acetate/toluene, 2:8), the product of the title is obtained.

It is recrystallized in isopropanol.
Yield: 35%
Melting point: 128°-129° C.
Spectral characteristics:
Infrared: 3030-2960 cm$^{-1}$: $\nu$(CH); 1680 cm$^{-1}$: $\nu$(C=O); 1585 cm$^{-1}$: $\nu$(C=C).

Nuclear magnetic resonance: $\delta$ ppm: solvent: CDCl$_3$; $\delta$=1.07 triplet; 3H; CH$_3$ (butyl); $\delta$=1.85 multiplet, 2H, CH$_2$—CH$_3$; $\delta$=2.74 singlet; 1H, CH$_3$; $\delta$=3.26 triplet; 2H, CO—CH$_2$.

Using the procedure described in Example 52, but using 5-methyl-2-phenyloxazolo[4,5-b]pyridine as a starting material, the following is obtained:
2-PHENYL-5-METHYL-7-BUTYRYLOXAZOLO[4,5-b]PYRIDINE (EXAMPLE 53).

EXAMPLE 54

2-(2-FLUOROPHENYL)-6-BUTYRYLOXAZOLO[5,4-b]PYRIDINE

Using the procedure described in Example 1, but replacing 2-phenyloxazolo[4,5-b]pyridine by 2-(2-fluorophenyl)oxazolo[5,4-b]pyridine (J. Med. Chem. 1978, 21, 11, 1158+) and using 8.4 ml of concentrated sulfuric acid in 16.8 ml of water and 16.8 ml of acetic acid, and after purification on a column of silica (40 to 63μ; 70-230 mesh; eluent: ethyl acetate/toluene, 1:9), the product of the title is obtained.

Yield: 30%
Melting point: 102°-103° C.
Spectral characteristics: $^1$H NMR, solvent: CDCl$_3$ $\delta$(ppm); $\delta$=1.08: 3H, triplet; CH$_3$; $\delta$=1.86: 2H, multiplet; CH$_2$—CH$_3$; $\delta$=3.5: 2H, triplet; CO—CH$_2$; $\delta$=7.27-7.66: 3H, complex, H$_{3'}$, H$_{4'}$, H$_{5'}$; $\delta$=7.82: 1H, doublet; H$_6$, J=5 Hz; $\delta$=8.33 ppm: 1H, multiplet; H$_{6'}$; $\delta$=8.49 ppm: 1H, doublet; H$_7$, J=5 Hz.

Infrared: $\nu$(cm$^{-1}$): 3080-2960: $\nu$(CH); 1680: $\nu$(CO); 1590: $\nu$(C=C).

EXAMPLE 55

2-(2-FLUOROPHENYL)-4-BUTYRYLOXAZOLO[5,4-b]PYRIDINE

STAGE A: 3-(2-FLUOROBENZOYLAMINO)-2-CHLOROPYRIDINE 4.44 g (28 mmol) of 2-fluorobenzoyl chloride are added to 30 ml of anhydrous pyridine at 0° C. while the temperature is maintained below 5° C. 3 g of 3-amino-2-chloropyridine in 20 ml of pyridine are added with stirring using a pressure equalizing funnel. After being left overnight at room temperature, the reaction medium is poured into an ice/water mixture. The solid obtained is filtered off and washed several times with water.

Yield: 96%
Melting point: 122° C.

STAGE B: 2-CHLORO-3-(2-FLUOROBENZOYLAMINO)-4-BUTYRYLPYRIDINE

Using the procedure described in Examples 1 and 2, but replacing 2-phenyloxazolo[4,5-b]pyridine by 3-(2-fluorobenzoylamino)-2-chloropyridine and using 1.5 ml of concentrated sulfuric acid in 7.5 ml of water and 25 ml of acetic acid, and after the separation of 2-chloro-3-(2-fluorobenzoylamino)-6-butyrylpyridine, the expected product is obtained.

Yield: 25%
Melting point: 142° C.
Spectral characteristics: $^1$H NMR, solvent: CDCl$_3$ $\delta$(ppm): $\delta$=1.00: 3H, triplet; CH$_3$; $\delta$=1.76: 2H, multiplet; CH$_2$—CH$_3$; $\delta$=3.13: 2H, triplet; CO—CH$_2$; $\delta$=7.2-7.65: 3H, multiplet, H$_{3'}$, H$_{4'}$, H$_{5'}$; $\delta$=8.07: 1H, doublet; H$_6$, J=8.2 Hz; $\delta$=8.20: 1H, multiplet; H$_{6'}$; $\delta$=9.10: 1H, doublet; H$_5$, J=8.2 Hz; $\delta$=9.4: 1H, complex; NH—CO.

Infrared: $\nu$(cm$^{-1}$): 3400: $\nu$(NHCO); 2960: $\nu$(CH); 1685: $\nu$(CO); 1665: $\nu$ CO (NHCO).

STAGE C: PREPARATION OF THE SOLUTION OF TRIMETHYLSILYL POLYPHOSPHATE (PPSE)

2.5 g (8.75 mmol) of phosphorus pentoxide and 6.25 ml (33 mmol) of hexamethyldisiloxane are brought to reflux under an inert atmosphere in 12.5 ml of anhydrous 1,2-dichlorobenzene until a clear solution is obtained.

STAGE D: 2-(2-FLUOROPHENYL)-4-BUTYRYLOXAZOLO[5,4-b]PYRIDINE 1.4 g (8 mmol) of 3-(2-fluorobenzoylamino)-2-chloro-4-butyrylpyridine, obtained in stage B, are added to the solution of PPSE prepared in stage C. The mixture is brought to reflux of the 1,2-dichlorobenzene for 40 hours. After evaporation of the solvent under vacuum, an ice/water mixture is added, sodium bicarbonate is added until a pH of 7 is obtained and the product is extracted with dichloromethane. It is purified by passage through a column of silica (40 to 63μ; 70-230 mesh; eluent: ethyl acetate/toluene, 5:95).

Yield: 70%.

Melting point: 124°-125° C.

Spectral characteristics: $^1$H NMR, solvent: CDCl$_3$ δ(ppm): δ=1.05: 3H, triplet; CH$_3$; δ=1.80: 2H, multiplet; CH$_2$—CH$_3$; δ=3.26: 2H, triplet; CO—CH$_2$; δ=7.26-7.66: 3H, multiplet, H$_{3'}$, H$_{4'}$, H$_{5'}$; δ=8.22: 2H, singlet; H$_5$H$_6$; δ=8.30: 1H, multiplet; H$_6$.

Infrared: ν(cm$^{-1}$): 3060-2960: ν(CH); 1685: ν(CO); 1590: ν(C=C).

PHARMACOLOGICAL STUDY OF THE COMPOUNDS OF THE INVENTION

EXAMPLE A

Study of the acute toxicity

The acute toxicity was assessed after oral administration to batches of 8 mice (26±2 grams). The animals were observed at regular intervals during the first day, and daily during the 2 weeks following the treatment. The LD$_{50}$, the dose causing the death of 50% of the animals, was evaluated.

The LD$_{50}$ of the test products is greater than 1000 mg/kg for all the compounds studied, which indicates the low toxicity of the compounds of the invention.

EXAMPLE B

Study of the analgesic activity

The activity against pain was investigated in mice (23-25 g) according to a protocol derived from the technique described by SIEGMUND (SIEGMUND E.A., R. A. CADMUS & GOLU, J. Pharm. Exp. Ther. 119, 184, 1957). The mice, randomized in batches of 12 animals, received the treatment orally (excipient for the controls) 1 hour before the intraperitoneal injection of a 0.02% aqueous-alcoholic solution of phenyl-p-benzoquinone (Sigma). The writhing movements are counted between the 5th and 10th minute after injection.

The percentage activity obtained was evaluated for each dose (% decrease in the number of writhing movements in the treated animals relative to the controls). An ED$_{50}$, the dose producing a 50% activity, was determined for each product.

It was apparent that the compounds of the invention possess a very advantageous analgesic activity.

Thus, the ED$_{50}$ of the compound of Example 6 is in the region of 8 mg.kg$^{-1}$; the ED$_{50}$ of that of Example 2 is in the region of 5 mg.kg$^{-1}$.

By way of comparison, the ED$_{50}$ of the product of Example 6 (2-(2-fluorophenyl)oxazolo[4,5-b]pyridine) of U.S. Pat. No. 4,038,396 in the same test is in the region of 12 mg.kg$^{-1}$.

EXAMPLE C: Study of the anti-inflammatory activity

The anti-inflammatory potential of the compounds was investigated on a model of acute inflammation induced by the subcutaneous injection of a solution of carrageenan into the rat hind foot, according to a technique based on the method of WINTER, C.A., E. A. RISLEY and G. N. NUSS (Proc. Soc. Exp. Med. 111, 554, 1962). The rats (100-120 g), randomized in batches of 8, were treated (including the controls, which receive excipient) 1 hour before the local injection of a 0.5% suspension of carrageenan (Sigma type IV; 0.1 ml per rat). The edema is determined 3 hours after injection, by plethysmometric measurement (UGO BASILE water plethysomometer) of the volume of each of the hind feet (edema=volume of the inflamed foot-volume of the non-inflamed foot).

The percentage activity corresponds to the percentage decrease in the mean edema of the batch compared with the mean of the corresponding control batch. An ED$_{30}$, the dose producing a 30% activity, was determined.

This ED$_{30}$ is equal to 50 mg.kg$^{-1}$ for the compound of Example 6 of U.S. Pat. No. 4,038,396. It is very markedly greater than 50 mg.kg$^{-1}$ for all the compounds of the invention.

The pharmacological study of the products of the invention hence shows that the latter are of low toxicity, endowed with an analgesic activity more intense than that of the compounds of related structure of the prior art, and devoid of anti-inflammatory activity in contrast to these same compounds of the prior art.

EXAMPLE D

Pharmaceutical composition: TABLET

Tablets containing 25 mg of 2-(2-fluorophenyl)-7-butyryloxazolo[4,5-b]pyridine

Preparation formula for 100 tablets.

| | |
|---|---|
| 2-(2-Fluorophenyl)-7-butyryloxazolo-[4,5-b]pyridine | 25 g |
| Wheat starch | 15 g |
| Corn starch | 15 g |
| Lactose | 65 g |
| Magnesium stearate | 2 g |
| Silica | 1 g |
| Hydroxypropylcellulose | 2 g |

TABLE 1

| | SPECTRAL CHARACTERISTICS OF EXAMPLES Nos. 1 TO 11 (see appended formula of the compounds) | | |
|---|---|---|---|
| EX | POSITION OF THE n-BUTYRYL | INFRARED | NUCLEAR MAGNETIC RESONANCE |
| | RA' RC | | |

TABLE 1-continued

SPECTRAL CHARACTERISTICS OF EXAMPLES Nos. 1 TO 11
(see appended formula of the compounds)

| EX | POSITION OF THE n-BUTYRYL | | | INFRARED | | NUCLEAR MAGNETIC RESONANCE | |
|---|---|---|---|---|---|---|---|
| 1 | 5 | H | H | 3000–2860: | v CH | $\delta$: 1.125; t; 3H; $CH_3$; J=7.5Hz | $\delta$: 1.873; m; 2H: $\underline{CH_2}$—$CH_3$ |
| | | | | 1680: | v CO | $\delta$: 3.25; t; 2H; CO—$\underline{CH_2}$— | $\delta$: 7.50–7.70; m; 3H; $H_B$; $H_C$; $H_{B'}$ |
| | | | | | conjugated | $\delta$: 8.05; d; 1H; $H_7$ | $\delta$: 8.20–8.25; m; 3H; $H_A$, $H_{A'}$, $H_6$ |
| 2 | 7 | H | H | 3000–2860: | v CH | $\delta$: 1.125; t; 3H; $CH_3$; J=7.5Hz | $\delta$: 1.873; m; 2H: $\underline{CH_2}$—$CH_3$ |
| | | | | 1680: | v CO | $\delta$: 3.25; t; 2H; CO—$\underline{CH_2}$ | $\delta$: 7.45–7.75; m; 3H; $H_B$; $H_C$; $H_{B'}$ |
| | | | | | conjugated | $\delta$: 7.72; d; 1H; $H_6$; J=5Hz | $\delta$: 8.25; m; 2H; $H_A$; $H_{A'}$ |
| | | | | | | $\delta$: 8.60; d; 1H; J=5Hz; $H_5$ | |
| 3 | 5 | H | Cl | 3000–2860: | v CH | $\delta$: 1.125; t; 3H; $CH_3$; J=7.4Hz | $\delta$: 1.875; m; 2H: $\underline{CH_2}$—$CH_3$ |
| | | | | 1680: | v CO | $\delta$: 3.25; t; 2H; CO—$\underline{CH_2}$ | $\delta$: 7.58; 2H; d; J=8.7Hz; HB, HB' |
| | | | | | conjugated | $\delta$: 8.05; d; 1H; $H_7$ | $\delta$: 8.20; 2H$H_6$; $H_A$ |
| 4 | 7 | H | Cl | 3000–2860: | v CH | $\delta$: 1.125; t; 3H; $CH_3$; J=7.4Hz | $\delta$: 1.875; m; 2H: $\underline{CH_2}$—$CH_3$ |
| | | | | 1680: | v CO | $\delta$: 3.25; t; 2H; CO—$\underline{CH_2}$; J=7Hz | $\delta$: 7.58; 2H; d; J=8.7Hz; $H_B$, $H_{B'}$ |
| | | | | | conjugated | $\delta$: 7.70; d; 1H; $H_6$; J=5Hz | $\delta$: 8.25; 2H; J=8.7Hz; $H_A$; $H_{B'}$ |
| | | | | | | $\delta$: 8.60; d; 1H; $H_6$; J=5Hz | |
| 5 | 5 | F | H | 3000–2860: | v CH | $\delta$: 1.125; t; 3H; $CH_3$; J=7.5Hz | $\delta$: 1.873; m; 2H: $\underline{CH_2}$—$CH_3$ |
| | | | | 1680: | v CO | $\delta$: 7.27–7.68; m; 3H; $H_B$; $H_{B'}$; $H_C$ | $\delta$: 3.25; t; 2H; J=7.5 H2; CO—$\underline{CH_2}$ |
| | | | | | conjugated | $\delta$: 8.22; 1H; d; J=8.4Hz; $H_6$ | $\delta$: 8.02; 1H; d; J=8.4 H2; $H_7$ |
| | | | | | | | $\delta$: 8.38; 1H; m; $H_A$ |
| 6 | 7 | F | H | 3000–2860: | v CH | $\delta$: 1.11; t; 3H; $CH_3$; J=7.4Hz | $\delta$: 1.80; m; 2H: $\underline{CH_2}$—$CH_3$ |
| | | | | 1680: | v CO | $\delta$: 3.46; t; 2H; CO—$\underline{CH_2}$; J=7.4Hz | $\delta$: 7.68–7.27 m; 3H; $H_B$; $H_{B'}$; $H_{C'}$ |
| | | | | | conjugated | $\delta$: 7.76; d; 1H; J=5.5Hz; $H_6$ | $\delta$: 8.4; m; 1H; $H_A$ |
| | | | | | | $\delta$: 8.75; d; 1H; J=5.5Hz; $H_5$ | |
| 7 | 5 | Cl | H | 3000–2860: | v CH | $\delta$: 1.12; t; 3H; $CH_3$; J=7.5Hz | $\delta$: 1.875; m; 2H: $\underline{CH_2}$—$CH_3$ |
| | | | | 1680: | v CO | $\delta$: 3.25; t; 2H; J=7.5Hz; $\underline{CH_2}CH_3$ | $\delta$: 7.25–7.70; m; 2H; $H_B$; $H_{B'}$; $H_C$ |
| | | | | | conjugated | $\delta$: 8.02; 1H; d; J=8.4Hz; $H_7$ | $\delta$: 8.22; 1H; d; J=8.4Hz-$H_B$ |
| | | | | | | $\delta$: 8.38; 1H; m; $H_A$ | |
| 8 | 7 | Cl | H | 3000–2860: | v CH | $\delta$: 1.11; t; 3H; $CH_3$; J=7.4Hz | $\delta$: 1.80; m; 2H: $\underline{CH_2}$—$CH_3$ |
| | | | | 1680: | v CO | $\delta$: 3.46; t; 2H; CO—$\underline{CH_2}$; J=7.4Hz | $\delta$: 7.70–7.25 ppm; 3H; $H_B$, $H_{B'}$; $H_C$ |
| | | | | | conjugated | $\delta$: 7.75; d; 1H; $H_6$ | $\delta$: J=8.40Hz; m; 1H; HA |
| | | | | | | $\delta$: 8.75; d; 1H | |
| | | RA | RA' | | | | |
| 10 | 7 | Cl | Cl | 3080–2880: | v CH | 1.06 ppm: 3H; t; $CH_3$ | 1.92 ppm; 2H; m; $\underline{CH_2}$—$CH_3$ |
| | | | | 1690: | v CO | 3.20 ppm: 2H; t; CO—$\underline{CH_2}$ | 7.51 ppm; 3H; m; Hb; HbHb'Hc |
| | | | | 1625: | v C=C | 7.85 ppm: 1H; d; H6, J=6Hz | 8.81 ppm; 1H; d; H5; J=6Hz |
| 11 | 7 | F | F | 3070–2960: | v CH | 1.08 ppm: 3H; t; $CH_3$ | 1.86 ppm; 2H; m; $\underline{CH_2}$—$CH_3$ |
| | | | | 1685: | v CO | 3.27 ppm: 2H; t; CO—$\underline{CH_2}$ | 7.17 ppm; 1H; t; Hc |
| | | | | 1590: | v C=C | 7.6 ppm: 2H; 2dd; Hb; Hb'; J1=2.5Hz, J2=6Hz | |
| | | | | | | 7.81 ppm; 1H; d; H6; J=5Hz | |
| | | | | | | 8.80 ppm; 1H; d; H5; H=5Hz | |

$\delta$: ppm; s: singlet; d: doublet; dd: doublet of doublet; t: triplet; m: multiplet; Ra = H  Rc = H

TABLE 2

SPECTRAL CHARACTERISTICS OF EXAMPLES Nos. 13 TO 16
(see appended formula of the compounds)

| EX | POSITION OF THE BENZOYL | RA' | RC | INFRARED | | NUCLEAR MAGNETIC RESONANCE |
|---|---|---|---|---|---|---|
| 13 | 5 | F | H | 3080–30: | v CH | 7.27–7.68 ppm; m; 6H; $H_B$; $H_{B'}$; $H_C$; $H_B$; $H_{B'}$'$H_Y$ |
| | | | | 1645: | v CO | 8.09 ppm; d; 1H; J=8.6Hz; $H_7$ |
| | | | | | conjugated | 8.19–8.27 ppm; m; 3H; $H_6$; $H_\alpha$, $H_{\alpha'}$ |
| | | | | | | 8.36 ppm; m; 1H; $H_A$ |
| 14 | 7 | F | H | 3080–30: | v CH | 7.19–7.96; m; aromatiques |
| | | | | 1645: | v CO | 8.22; 1H; m; $H_A$ |
| | | | | | conjugated | 8.79; 1H; d; J=3.9Hz; $H_6$ |
| 15 | 5 | Cl | H | 3080–30: | v CH | 7.20–7.70; m; 6H; $H_B$; $H_{B'}H_C$; $H_B$; $H_{B'}$; $H_Y$ |
| | | | | 1645: | v CO | 8.10; d; 1H; J=8.6Hz; $H_7$ |
| | | | | | conjugated | 8.19–8.30 ppm; m; 3H; $H_6$; $H_\alpha$, $H_{\alpha'}$ |
| | | | | | | 8.4 ppm; m; 1H; $H_A$ |

TABLE 2-continued
SPECTRAL CHARACTERISTICS OF EXAMPLES Nos. 13 TO 16
(see appended formula of the compounds)

| EX | POSITION OF THE BENZOYL | RA' | RC | INFRARED | NUCLEAR MAGNETIC RESONANCE |
|---|---|---|---|---|---|
| 16 | 7 | Cl | H | 3080–30: ν CH<br>1645: ν CO<br>conjugated | 7.15–8.00; m; aromatiques<br>8.20; 1H; m; $H_4$<br>8.79; 1H; d; J=3.9Hz; $H_6$ |

δ: ppm; s: singlet; d: doublet; t: triplet; m: multiplet; Ra=H

APPENDIX

1. FORMULA OF THE COMPOUNDS OF TABLE 1, PAGES 21 TO 23

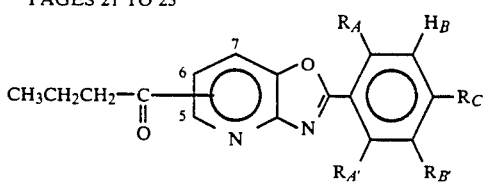

2. FORMULA OF THE COMPOUNDS OF TABLE 2, PAGE 24

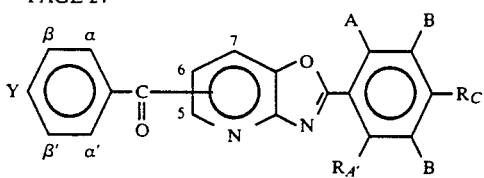

3. NOMENCLATURE

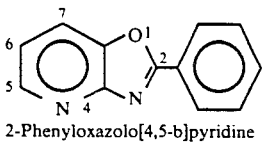

2-Phenyloxazolo[4,5-b]pyridine

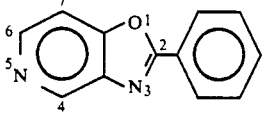

2-Phenyloxazolo[4,5-c]pyridine

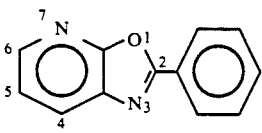

2-Phenyloxazolo[5,4-b]pyridine

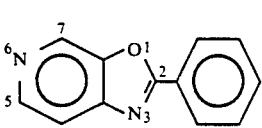

2-Phenyloxazolo[5,4-c]pyridine

We claim:
1. A compound selected from those of formula (I):

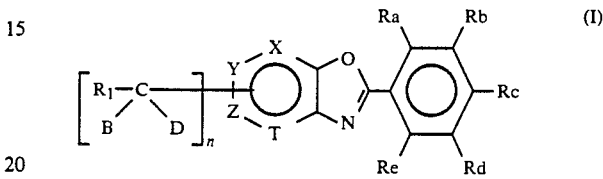

in which:

X, Y, Z and T each represent, independently of one another, a nitrogen atom, a —CH= group or a group CW= or CV=, in which W and V, which may be identical or different, represent a halogen atom or a lower alkyl or lower alkoxy group optionally substituted with one or more halogen atoms, on condition that only one of them represents a nitrogen atom, Ra, Rb, Rc, Rd and Re represent, independently of one another, a hydrogen atom, a halogen atom or a lower alkyl group optionally substituted with one or more halogen atoms, n represents 1 or 2, B represents a hydrogen atom and D a hydroxyl group, or B and D simultaneously represent an oxygen atom, and $R_1$ represents a hydrogen atom, a linear or branched lower alkyl, linear or branched lower alkenyl, aryl, heteroaryl or lower arylalkyl group, a cycloalkyl group having 3 to 7 carbon atoms or a cycloalkylalkyl group, it being possible for each of the lower alkyl, lower alkenyl, aryl, lower arylalkyl, cycloalkyl and cycloalkylalkyl groups to be substituted with one or more halogen atoms or a lower alkyl or lower alkoxy group optionally substituted with one or more halogen atoms, their isomers, epimers and diastereoisomers, as well as their addition salts with a pharmaceutically-acceptable acid.

2. A compound as claimed in claim 1 in which n represents 1.

3. A compound as claimed in claim 1 in which n represents 1 and T represents a nitrogen atom, X, Y and Z each represent a —CH= group or a group —CW= or —CV=, the group $R_1$—C—(BD) being bound to one of the carbons X or Z.

4. A compound as claimed in claim 1 in which n represents 1 and X represents a nitrogen atom, and Y, Z and T each represent a —CH= group or a group —CW= or —CV=, the group $R_1$—C(BD) being bound to one of the carbons X or Z.

5. A compound as claimed in claim 1 in which B and D simultaneously represent an oxygen atom.

6. A compound as claimed in claim 1 in which B represents a hydrogen atom and D represents a hydroxyl group.

7. A compound as claimed in claim 1 in which $R_1$—C(BD) represents a butyryl group.

8. A compound as claimed in claim 1 in which $R_1$—C(BD) represents a benzoyl group.

9. A compound as claimed in claim 1, which is selected from 2-(2-fluorophenyl)-7-butyryloxazolo[4,5-b]pyridine and an addition salt thereof with a pharmaceutically-acceptable acid.

10. A compound as claimed in claim 1, which is selected from 2-(2-fluorophenyl)-5-butyryloxazolo[4,5-b]pyridine and an addition salt thereof with a pharmaceutically-acceptable acid.

11. A compound as claimed in claim 1, which is selected from 2-(2-fluorophenyl)-4-butyryloxazolo[5,4-b]pyridine and an addition salt thereof with a pharmaceutically-acceptable acid.

12. A compound as claimed in claim 1, which is selected from 2-(2-fluorophenyl)-6-butyryloxazolo[5,4-b]pyridine and an addition salt thereof with a pharmaceutically-acceptable acid.

13. A pharmaceutical composition useful in treating pain containing, as active principle, a compound of claim 1 in combination with a pharmaceutically-acceptable, vehicle or excipient.

14. A method for treating a living animal afflicted with pain comprising the step of administering to the said living animal an amount of a compound of claim 1 which is suitable for the alleviation of said condition.

15. A compound of claim 1 wherein at least one of $R_a$, $R_b$, $R_c$, $R_d$, and $R_e$ represents a trifluoromethyl group.

16. A compound of claim 1 wherein the radical $R_1$ comprises a trifluoromethyl group.

17. A compound of claim 1 wherein at least one of W and V represents a trifluoromethyl group.

* * * * *

UNITED STATES PATENT AND TRADEMARK OFFICE
CERTIFICATE OF CORRECTION

PATENT NO. : 5,061,713

DATED : Oct. 29, 1991

INVENTOR(S) : Gérald Guillaumet, Christine Flouzat, Jacqueline Bonnet

It is certified that error appears in the above-identified patent and that said Letters Patent is hereby corrected as shown below:

Column 5, line 46; "2-(2-FLUOROPHENYL)-b"
  should read -- 2-(2-FLUOROPHENYL)- --.
Column 7, lines 42 & 43; the close parenthesis should be moved to the preceeding line and placed inside of the hyphen.
Column 8, line 15/16; the close bracket should be moved to the preceding line and placed inside of the hyphen.
Column 8, line 19/20; the close bracket should be moved to the preceding line and placed inside of the hyphen.
Column 8, line 23/24; the "Y)" should be moved to the preceding line and placed inside of the hyphen.
Column 8, line 27/28; the "Y)" should be moved to the preceding line and placed inside of the hyphen.
Column 14, Table 1-continued, EX 2, first line, last column; "$\underline{CH_2-CH_3}$" should read -- $\underline{CH_2-CH_3}$ --.
Column 14, Table 1-continued, EX 5, fourth line, last column; "m:" should read -- m; --.
Column 18, line 6; delete the comma after "able".(R&A 4-22-91,P.4)

Signed and Sealed this

Thirteenth Day of April, 1993

*Attest:*

STEPHEN G. KUNIN

*Attesting Officer*         *Acting Commissioner of Patents and Trademarks*